(12) United States Patent
Liu et al.

(10) Patent No.: US 12,048,502 B2
(45) Date of Patent: Jul. 30, 2024

(54) SURGERY ROBOT SYSTEM AND USE METHOD THEREFOR

(71) Applicant: SINOVATION (BEIJING) MEDICAL TECHNOLOGY CO., LTD, Beijing (CN)

(72) Inventors: Wenbo Liu, Beijing (CN); Chenlong Chu, Beijing (CN); Li Wen, Beijing (CN); Qi Qi, Beijing (CN)

(73) Assignee: SINOVATION (BEIJING) MEDICAL TECHNOLOGY CO., LTD, Beijing (CN)

( * ) Notice: Subject to any disclaimer, the term of this patent is extended or adjusted under 35 U.S.C. 154(b) by 363 days.

(21) Appl. No.: 17/424,833

(22) PCT Filed: Jan. 17, 2020

(86) PCT No.: PCT/CN2020/072829
§ 371 (c)(1),
(2) Date: Jul. 21, 2021

(87) PCT Pub. No.: WO2020/151598
PCT Pub. Date: Jul. 30, 2020

(65) Prior Publication Data
US 2022/0022985 A1 Jan. 27, 2022

(30) Foreign Application Priority Data
Jan. 21, 2019 (CN) .......................... 201910052855.1

(51) Int. Cl.
*A61B 34/37* (2016.01)
*A61B 34/20* (2016.01)
(Continued)

(52) U.S. Cl.
CPC .............. *A61B 34/37* (2016.02); *A61B 34/20* (2016.02); *G06T 7/521* (2017.01); *G06T 7/70* (2017.01);
(Continued)

(58) Field of Classification Search
CPC ......... A61B 34/37; A61B 34/20; G06T 7/521; G06T 7/70
See application file for complete search history.

(56) References Cited

U.S. PATENT DOCUMENTS

2013/0345718 A1* 12/2013 Crawford ........... A61B 17/8866
606/130
2014/0276935 A1 9/2014 Yu
(Continued)

FOREIGN PATENT DOCUMENTS

| CN | 103337071 A | 10/2013 |
|---|---|---|
| CN | 10797006 A | 5/2018 |
| CN | 109549705 A | 4/2019 |

OTHER PUBLICATIONS

International Search Report of PCT/CN2020/072829.
Written Opinion of PCT/CN2020/072829.

*Primary Examiner* — Hugh Maupin

(57) ABSTRACT

The present invention provides a surgical robot system which includes a workstation, a robotic arm, a scanning module, a guiding module and the like. Fast registration may be completed by means of the scanning module. The system improves the speed and accuracy of registration and shortens the period of the operation.

3 Claims, 11 Drawing Sheets

(51) Int. Cl.
*G06T 7/521* (2017.01)
*G06T 7/70* (2017.01)
*A61B 34/10* (2016.01)
*A61B 90/00* (2016.01)

(52) U.S. Cl.
CPC ... *A61B 2034/105* (2016.02); *A61B 2034/107* (2016.02); *A61B 2034/2051* (2016.02); *A61B 2034/2055* (2016.02); *A61B 2034/2065* (2016.02); *A61B 2034/2072* (2016.02); *A61B 2090/064* (2016.02); *G06T 2207/10028* (2013.01); *G06T 2207/30004* (2013.01); *G06T 2207/30244* (2013.01)

(56) References Cited

U.S. PATENT DOCUMENTS

| | | | | |
|---|---|---|---|---|
| 2015/0182288 | A1* | 7/2015 | Greenwald | A61B 34/20 606/279 |
| 2016/0184032 | A1* | 6/2016 | Romo | B25J 9/1682 901/46 |
| 2018/0014891 | A1* | 1/2018 | Krebs | A61B 5/055 |
| 2020/0146754 | A1* | 5/2020 | Row | A61B 90/39 |
| 2021/0361357 | A1* | 11/2021 | Crawford | A61B 34/20 |

* cited by examiner

SURGERY ROBOT SYSTEM AND USE METHOD THEREFOR

CROSS-REFERENCE TO RELATED APPLICATIONS

This Application is a national stage application of PCT/CN2020/072829. The present application claims priorities from PCT Application No. PCT/CN2020/072829, filed Jan. 17, 2020, and from Chinese Patent Application No. 201910052855.1, filed on Jan. 21, 2019 and titled "SURGICAL ROBOT SYSTEM AND METHOD FOR USING THE SAME", which are incorporated herein by reference in its entirety.

TECHNICAL FIELD

The present invention relates to a technical field of medical devices, and in particular to a surgical robot system and a method for using the same.

BACKGROUND

The surgical robot system is a medical instrument developed in recent years that combines active and precise control of a robotic arm to a stereotaxic method, applied for brain biopsy, radio frequency/laser ablation, deep brain stimulation implantation, stereotaxic electroencephalographic electrode implantation positioned for an epileptic focus, craniotomy that requires navigation (removal of a tumor or an epileptic focus), a neuroendoscopic surgery (removal of a hamartoma, a brain cyst, a pituitary tumor or the like); the main steps for using the system includes preoperative planning, registration and the like. In the existing surgical robot system, a probe is used for registration. During the process of registration with the probe, it is necessary to guide the probe manually to a point to be matched, which is slow and time-assuming and there is a potential danger of injury caused by accidental contact. Therefore, it is necessary to provide solutions and systems that can solve these problems.

SUMMARY

In order to solve or alleviate at least one of the aforementioned existing problems, the present invention provides a surgical robot system which comprises:

a workstation, comprising a housing, a computation and control center, a display apparatus and an input device;

a robotic arm, comprising a plurality of arm segments which are connected by joints;

a scanning module, configured to collect information for a target space, wherein the target space is a part of a patient to be operated on, for example, a head; and a guiding module, configured to guide a surgical instrument to move in a desired trajectory;

wherein information collected by the scanning module is processed by the workstation to acquire three-dimensional information of the target space.

The scanning module of the surgical robot system of the present invention may include different composition structures in a first solution, the scanning module includes an image acquiring apparatus whose relative position relationship with the robotic arm is known, i.e., coordinates of the image acquiring apparatus in a coordinate system of the robotic arm may be acquired directly without being measured; the image acquiring apparatus may be a camera, for example, a monocular camera, a binocular camera or the like, and the robotic arm drives the image acquiring apparatus to acquire images at different locations so as to acquire three-dimensional information of the target space after calculation and reconstruction;

in a second solution, the scanning module includes a light emitting component and an image acquiring apparatus, wherein the light emitting component may emit light, such as infrared rays, to the target space, the image acquiring apparatus collects images, and the computation and control center calibrates the coordinates of the target space based on the acquired information after a sufficient number of point clouds are collected; and in a third solution, the scanning module includes a projecting component and an image acquiring apparatus, and the projecting component may emit a specific coded image to the target space and the image acquiring apparatus collects the image, thereby acquiring an accurate 3D structure of the target space by a corresponding decoding algorithm and then performing the registration. Compared with laser single point data collection in which only thousands of points within a limited range are collected, the collecting efficiency in the solution in which the projecting component emits specific coded images is greatly improved. During the same registration period, data collection may be fully covered within a square with a side length of dozens of centimeters, which greatly increases the range of data collection to acquire millions of data points and greatly increases the number of point clouds so as to improve the accuracy of the three-dimensional structure. The projecting component may not only emit a specific coded image but also project an image to the target space, for example, important physiological information of the patient, such as heartbeat, blood pressure and blood type, is projected onto the surface of the patient's skin to display the information in a non-contact and safe manner, and distortion correction may also be performed. The projecting component and the image acquiring apparatus of the scanning module have a predetermined relationship of relative spatial position. In one embodiment, the projecting component of the surgical robot system of the present invention includes a light source, a lens group, a digital micromirror device and a control module, and the image acquiring apparatus is a camera.

The scanning module of the surgical robot system of the present invention may be moved to a designated position by the robotic arm based on a known fixed position relative to an end of the robotic arm, or to a spatial position of the scanning module is determined by a tracking module.

The scanning module of the surgical robot system of the present invention may be an independent module which is used independently or connected to a robotic arm via a flange as a detachable part, and may also be an integrated module which is integrated at the end of the robotic arm. In case that the scanning module is an independent module, for example, the scanning module may be hand-held, however, the scanning module should include a marker (a traceable structure) and be used together with the tracking module; in case that the scanning module is a detachable module, the scanning module is connected to the robotic arm when in use, then the scanning module has known coordinates in a world coordinate system of the robotic arm. For example, in an embodiment, the scanning module projects a specific coded image to a target space, collects the image via an image acquiring apparatus, and acquires an accurate three-dimensional structure of the target space by a corresponding decoding algorithm. Image collection may be performed in a plurality of ways. For example, position of the robotic arm is adjusted to reacquire the image data of the target space according to software pre-loaded in the computation and control center according to the procedures set, and the previous data is combined in order to generate a three-dimensional structure. The above step may be performed many times until the three-dimensional image conforms to the requirements. Then, the three-dimensional structure matches with the three-dimensional model generated before the operation so that the operation area is converted to the coordinate system of the three-dimensional model. Then, the guiding module is used to replace the scanning module to continue the surgical steps. When the scanning module is integrated on the end of the robotic arm, the method for the scanning module to acquire the three-dimensional structure is the same with that for the detachable scanning module without using the flange so that a guiding structure may be mounted directly for subsequent surgical operation.

The marker may be assembled on a rigid structure to form a traceable structure, wherein the marker is arranged in a unique spatial distribution and can be used to determine a unique coordinate system.

The scanning module is controlled by the robotic arm for movement or used as an independent structure. Compared with the existing technology of collecting facial feature points for registration when a patient is only in a supine position, the constraint on the spatial position of the scanning module is reduced and the angles and positions for image collection are increased, which enables to collect full-head data which is difficult to acquire with the existing technologies. Moreover, it is not affected by a posture of a patient and a scope of the scanning image is expanded, thereby improving accuracy of the three-dimensional image and that of registration.

The surgical robot system of the present invention further includes a position tracking module which is configured to track a position of the scanning module. By tracking the spatial position of the scanning module when the scanning module is acquiring the image, the coordinate system of the image may be converted to construct a three-dimensional structure. Under the circumstance that the tracking module is included, the structure of the scanning module is the same as that mentioned above. The position tracking module may be implemented in a plurality of ways:

in a first situation, a position tracking module may be an image acquiring apparatus with a tracking ability, for example, a binocular camera. According to the principle of binocular imaging, the position of the tracked scanning module is acquired by acquiring a spatial position of a traceable marker (for example, a self-luminous marker, a corner point and the like) of the binocular camera, the traceable marker has a fixed spatial position relationship with the scanning module, and then the spatial position of the acquired image information may be determined by the position of the scanning module;

in a second situation, a position tracking module is an optical tracking apparatus which usually includes a light-traceable marker, a camera unit and a light emitting unit. Preferably, the light is infrared rays. The light-traceable marker is fixed to the scanning module, the infrared rays are projected to the marker by the light-emitting unit, and the reflected infrared rays are received by the camera unit. In this way, the position of the scanning module may be monitored in real time by the optical tracking apparatus. There may be a plurality of forms of light-traceable markers, for example, reflective balls having a special spatial position relationship, and reference mark consists of reflective balls; and in a third situation, a position tracking module is an electromagnetic tracking apparatus which determines the position of an electromagnetic marker by the influence of the electromagnetic marker in the magnetic field on the electromagnetic filed. By fixing the electromagnetic marker to the scanning module, the spatial position of the scanning module could be determined by the electromagnetic marker.

The robotic arm of the surgical robot system in the present invention has at least 6 degrees of freedom and the robotic arm is able to sense and measure the force applied thereto. In one embodiment, the robotic arm of the surgical robot system of the present invention has 6 joints and an end of the robotic arm is provided with a force sensor, thereby enabling the robotic arm to implement movement in 6 degrees of freedom, and the force sensor to sense the external force on the end of the robotic arm. In another embodiment, the robotic arm of the surgical robot system of the present invention has 7 joints and each joint has a torque sensor, thereby enabling the robotic arm to move in 7 degrees of freedom. In response to that the position of the end of the robotic arm (the arm segment at the end) is not changed or a restricted movement is performed in a direction, postures of the joint and other arm segments may be adjusted for the convenience of the user. In yet another embodiment, the robotic arm has a motor only at a joint. The force on the joint can be calculated by a change in the current of the motor for adaptive adjustment. The robotic arm of the surgical robot system in the present invention may also have more than 6 joints, for example, 7, 8, 9 or 10 joints for more degrees of freedom.

Another aspect of the present invention further provides a method for using the surgical robot system according to the present invention, and the method include the following main steps:

a) using the surgical robot system to receive image data for visualized display, and making a surgical plan in the three-dimensional model;

b) using the scanning module to scan a target space, generating a three-dimensional structure with scanned data via the workstation, and registration with the image acquired in step a; and c) mounting the guiding module at an end of the robotic arm and executing the predetermined surgical plan.

Further, the scanning module is used in step b in one embodiment to scan the structure of the target space as follows: the user manually drags the robotic arm so that the scanning module reaches a desired position and acquires the scanning information. Moreover, scanning may be performed a plurality of times to acquire a full image of the target space. In another embodiment, the scanning module is used in step b to scan the structure of the target space as follows: at first, the scanning module is used to scan the target space for the first time to acquire an approximate position of the target space in the coordinate system, such as a lying position of a patient and an orientation of the patient's face; then, the workstation calculates an appropriate position for the scanning module to scan and plans an appropriate movement trajectory of the robotic arm based on parameters of the scanning module, and then a scanning step is executed automatically to control movement of the robotic arm and drive the scanning module to reach a predetermined position in a predetermined order. Data collection is performed to the target space from multiple angles so as to acquire a complete three-dimensional structure of the target space by decoding and splicing. During the process of projecting a specific coded image to the target space by the projecting component, scenes occlude each other due to limited projecting angles. As a result, a multi-angle collection is required to acquire a complete three-dimensional image.

The system of the present invention determines an accurate position of the scanning module via the tracking module, which ensures that an ideal three-dimensional structure can be acquired. Moreover, compared with the conventional point registration, it has obvious advantages in the speed of generating three-dimensional images, which shortens the period of an operation and reduces the risk of the operation.

Preferably, in another embodiment, the scanning module is mounted to the robotic arm via a flange before the registration in step b under the circumstance that the scanning module and the connectable guiding module are connected to the robotic arm in a detachable manner; the guiding module is used to replace the scanning module after the registration.

The guiding module is generally provided with a through hole and assists the surgical instruments to move in a certain direction. If necessary, the guiding module may be sterilized to meet the surgical requirements. Those skilled in the art should understand that other forms that can implement this function may also be adopted. Movement of the surgical instrument along a predetermined trajectory with the assistance of the guiding module means that the surgical instrument such as a guide wire, an electrode, a probe or the like moves in limited directions along an axial direction of the through hole in the through hole of the guiding module for the precise stereotaxy of the surgical instrument in the three-dimensional space.

The surgical robot system of the present invention may meet the requirements of the operating room, and the guiding module may be sterilized before being used.

BRIEF DESCRIPTION OF THE DRAWINGS

In order to more clearly illustrate the technical solutions of the specific embodiments of the present invention or the prior art, a brief introduction may be given hereinafter to the accompanying drawings that may be used in the description of the specific embodiments or the prior art. Obviously, the accompanying drawings in the description below are used for illustrating some embodiments of the present invention, and those of ordinary skill in the art may still derive other drawings from these accompanying drawings without creative efforts.

REFERENCE MARKS

100—workstation; 101—housing; 102—computation and control center; 103—display apparatus; 104—input device; 1011—wheel; 1012—fixing apparatus; 200—robotic arm; 300—scanning module; 400—guiding module; 500—tracking module; 201—base; 202—first joint; 203—first arm segment; 204—second joint; 205—second arm segment; 206—third joint; 207—third arm segment; 208—fourth joint; 209—fourth arm segment; 210—fifth joint; 211—fifth arm segment; 212—sixth joint; 213—sixth arm segment; 214—seventh joint; 215—seventh arm segment (end of robotic arm); 301—projecting component; 302—image acquiring apparatus; 303—traceable structure; 3031—traceable marker (spherical marker or corner point); 501—camera or projecting component; 502—camera; 503—infrared transmitting apparatus.

DETAILED DESCRIPTION

In order to make the objectives, technical solutions and advantages of the embodiments of the present invention clearer, the technical solutions of the present invention will be clearly and completely described below in conjunction with the accompanying drawings. Obviously, the described embodiments are only a part of the embodiments of the present invention, but not all of them. Based on the embodiments of the present invention, all other embodiments derived by those of ordinary skill in the art without creative efforts shall fall within the protection scope of the present invention.

To understand the embodiment of the embodiment, a surgical robot system disclosed in the present invention is introduced in detail at first.

Figure 1:
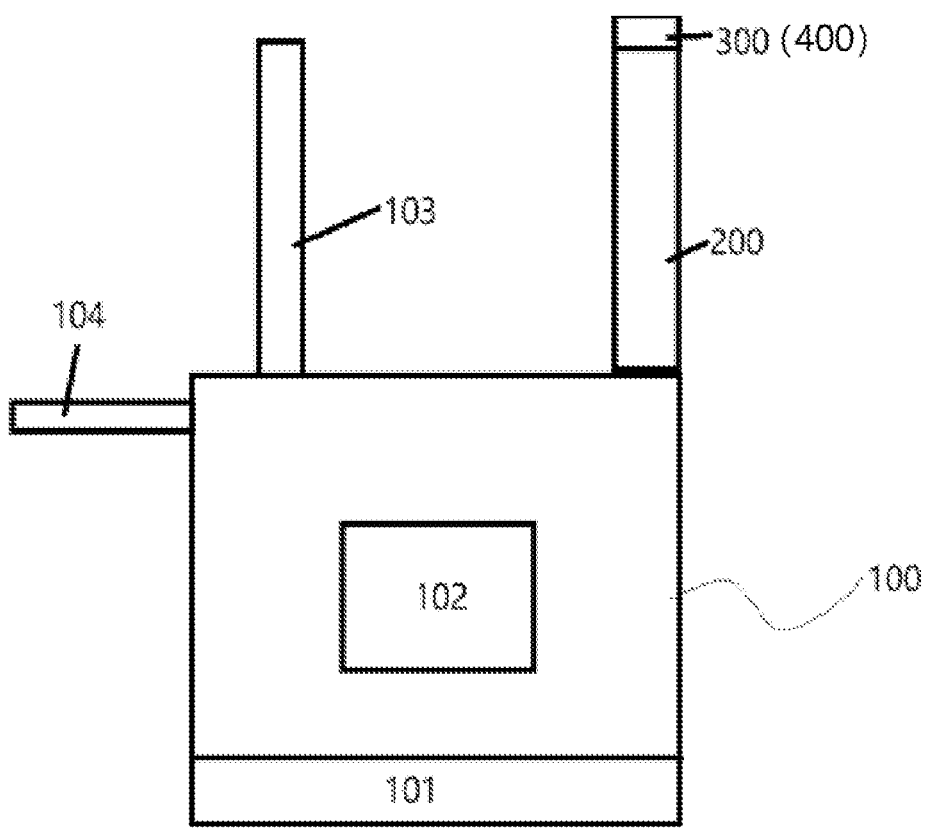
FIG. 1 is a structural schematic diagram of an embodiment according to a surgical robot system of the present invention.

With reference to FIG. 1, according to a schematic diagram of an embodiment of a surgical robot system of the present invention, the system includes a workstation 100, a robotic arm 200, a scanning module 300, and a guiding module 400, wherein:

the workstation 100 includes a housing 101, a computation and control center 102, a display apparatus 103, and an input device 104; the computation and control center 102 communicates with the display apparatus 103, the input device 104 and other medical devices, for example, a magnetic resonance imaging (MRI) device or an X-ray computed tomography (CT) device, or a database. The display apparatus 103 is configured to display a three-dimensional image and a software control interface generated by the computation and control center 102. The number of display apparatuses may be more than one, and the display apparatus may also be one of other existing devices, for example, an LCD display, a notebook computer, a tablet computer, a smart phone or the like. In one embodiment, a touch screen with both display and input functions may be used; in another embodiment, the display apparatus 103 may be a glass with a function of projecting display or a helmet with a projection screen, for the convenience of the user. The input device 104 is any input accessory, for example, a foot switch, a touch pad, a touch pen, a touch screen, a joystick, a trackball, a wireless mouse, a mouse, a keyboard, a voice input port or a combination thereof, which allows the user to input an order to the computation and control center 102; the input device 104 may be omitted under the circumstance that the display apparatus 103 has an input function. The housing 101 has a wheel, a fixing apparatus and a handle, which ensures that the user can easily move the workstation 100; the housing 101 may also have a connecting apparatus which connects the workstation 100 and an operating table/head frame or the like in a fixed manner. The robotic arm 200 is any robotic arm having at least 6 degrees of freedom, for example, it may be the robotic arm having 7, 8, 9 or 10 degrees of freedom and an end of the robotic arm is connected to the work station 100 in a fixed manner.

The scanning module 300 may have a plurality of structures. In a first solution, the scanning module only includes an image acquiring apparatus, for example, a binocular camera or the like; in a second solution, the scanning module includes a light emitting component and an image acquiring apparatus, wherein the light emitting component emits light to the target space, the image acquiring apparatus collects images, and the computation and control center calibrates the coordinates of the target space based on the acquired information after sufficient data is collected; and in a third solution, the scanning module includes a projecting component and an image acquiring apparatus, and the projecting component and the image acquiring apparatus of the scanning module have a predetermined relationship of relative spatial position. The projecting component may not only emit a specific coded image but also project an image to the target space. For example, important physiological information of the patient, such as heartbeat, blood pressure and blood type, is projected onto the surface of the patient's skin to display the information in a non-contact and safe manner, and distortion correction may also be performed. The scanning module 300 may be independent, connected to the robotic arm 200 in a detachable manner or integrated in the robotic arm 200. FIG. 1 shows the scanning module 300 which is connected to the robotic arm 200 in a detachable manner.

A guiding module 400 may be connected to the end 215 of the robotic arm via a flange. The guiding module 400 includes a through hole through which another surgical instrument such as a guide wire, a drill bit, an electrode or the like may be guided and positioned; the surgical instrument reaches a specified position via the through hole of the guiding module based on the pre-planned path and length under the circumstance that the guiding module moves to a specified position and stays there.

The scanning module 300 is connected to the robotic arm 200. Since a relative position of the scanning module 300 and the robotic arm 200 is determined, the spatial position of the scanning module may be determined via the robotic arm 200. The scanning module acquires scanning data and transmits the data to the workstation 100 for processing. Next, registration is performed after a three-dimensional structure is established. And then, subsequent operation is performed by the guiding module 400.

Figure 2:
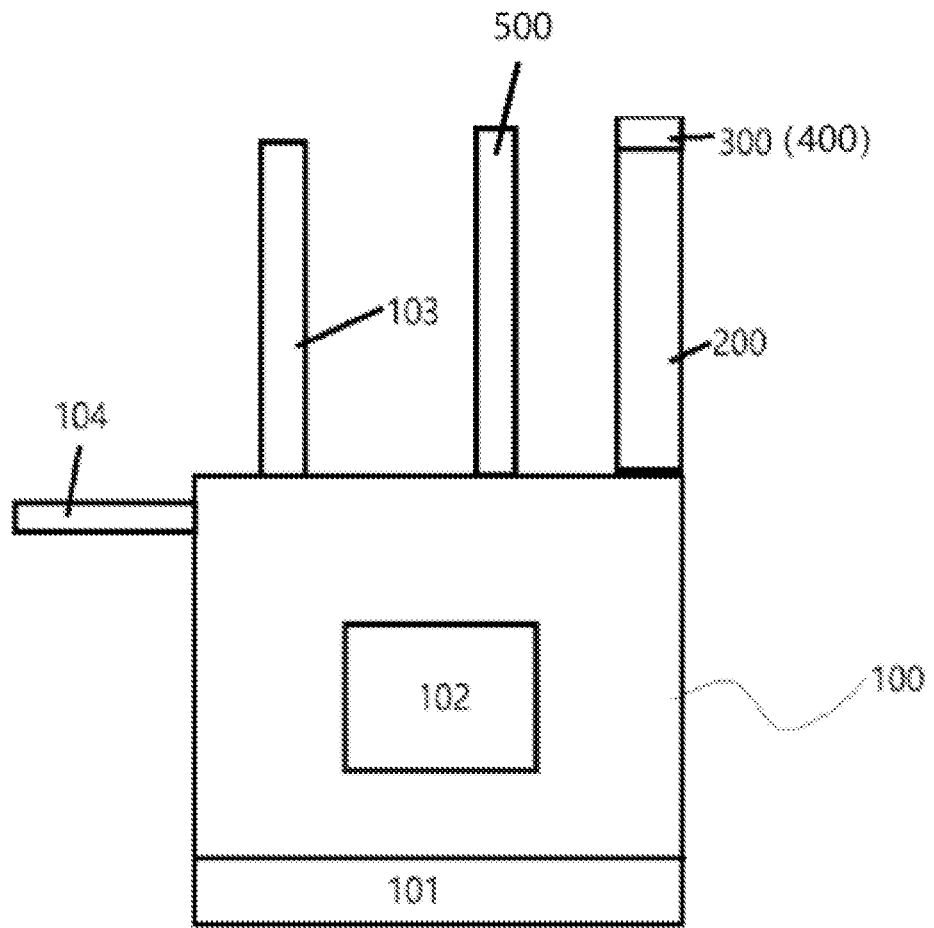
FIG. 2 is a structural schematic diagram of another embodiment according to a surgical robot system of the present invention.

With reference to FIG. 2, a schematic diagram of another embodiment according to a surgical robot system of the present invention, the system includes a workstation 100, a robotic arm 200, a scanning module 300, a guiding module 400, and a tracking module 500, wherein:

the workstation 100 includes a housing 101, a computation and control center 102, a display apparatus 103, and an input device 104; the computation and control center 102 communicates with the display apparatus 103, the input device 104 and other medical devices, for example, an MRI device, a CT device, or a database. The display apparatus 103 is configured to display a three-dimensional image and a software control interface generated by the computation and control center 102. The number of display apparatuses may be more than one, and the display apparatus may also be one of other existing devices, for example, an LCD display, a notebook computer, a tablet computer, a smart phone or the like. In one embodiment, a touch screen with both display and input functions may be used; in another embodiment, the display apparatus 103 may be a glass with a function of projecting display or a helmet with a projection screen, for the convenience of the user. The input device 104 is any input accessory, for example, a foot switch, a touch pad, a touch pen, a touch screen, a joystick, a trackball, a wireless mouse, a mouse, a keyboard, a voice input port or a combination thereof, which allows the user to input an order to the computation and control center 102; the input device 104 may be omitted under the circumstance that the display apparatus 103 has an input function. The housing 101 has a wheel, a fixing apparatus and a handle, which ensures that the user can easily move the workstation 100; the housing 101 may also have a connecting apparatus which connects the workstation 100 and an operating table/head frame or the like in a fixed manner. The robotic arm 200 is any robotic arm having at least 6 degrees of freedom, for example, it may be the robotic arm having 7, 8, 9 or 10 degrees of freedom and an end of the robotic arm is connected to the work station 100 in a fixed manner.

The scanning module 300 may have a plurality of structures. In a first solution, the scanning module only includes an image acquiring apparatus, for example, a binocular camera or the like; in a second solution, the scanning module includes a light emitting component and an image acquiring apparatus, wherein the light emitting component emits light to the target space, the image acquiring apparatus collects images, and the computation and control center calibrates the coordinates of the target space based on the acquired information after sufficient data is collected; and in a third solution, the scanning module includes a projecting component and an image acquiring apparatus, and the projecting component and the image acquiring apparatus of the scanning module have a predetermined relationship of relative spatial position. The projecting component may not only emit a specific coded image but also project an image to the target space. For example, important physiological information of the patient, such as heartbeat, blood pressure and blood type, is projected onto the surface of the patient's skin to display the information in a non-contact and safe manner, and distortion correction may also be performed. The scanning module 300 may be independent, connected to the robotic arm 200 in a detachable manner or integrated in the robotic arm 200. FIG. 2 shows the scanning module 300 which is connected to the robotic arm 200 in a detachable manner.

A guiding module 400 may be connected to the end 215 of the robotic arm via a flange. The guiding module 400 includes a through hole through which another surgical instrument such as a guide wire, a drill bit, an electrode or the like may be guided and positioned; the surgical instrument reaches a specified position via the through hole of the guiding module based on the pre-planned path and length under the circumstance that the guiding module moves to a specified position and stays there.

The tracking module 500 may be implemented by different devices as long as it may track a spatial position of the scanning module 300. For example, in a first situation, a position tracking module is a camera with a tracking ability, for example, a binocular camera. The scanning module includes corner points arranged in a special structure or self-luminous markers. According to the principle of binocular imaging, the position of the tracked scanning module is acquired, and then the spatial position of the acquired image information may be determined by the position of the scanning module; in a second situation, a position tracking module is an optical tracking apparatus which usually includes a light-traceable marker, a camera unit and a light emitting unit. Preferably, the light is infrared rays. The marker is fixed to the scanning module. In this way, the position of the scanning module may be monitored in real time by the optical tracking apparatus. There may be a plurality of forms of markers, for example, a ball and the like; and in a third situation, a position tracking module is an electromagnetic tracking apparatus which determines the position of an electromagnetic marker by the influence of the electromagnetic marker in the magnetic field on the electromagnetic filed, and the spatial position of the scanning module could be determined by the electromagnetic marker by fixing the electromagnetic marker to the scanning module. The tracking module 500 has a determined position relationship with the workstation 100 or the robotic arm 200.

Embodiment 1

Figure 3:
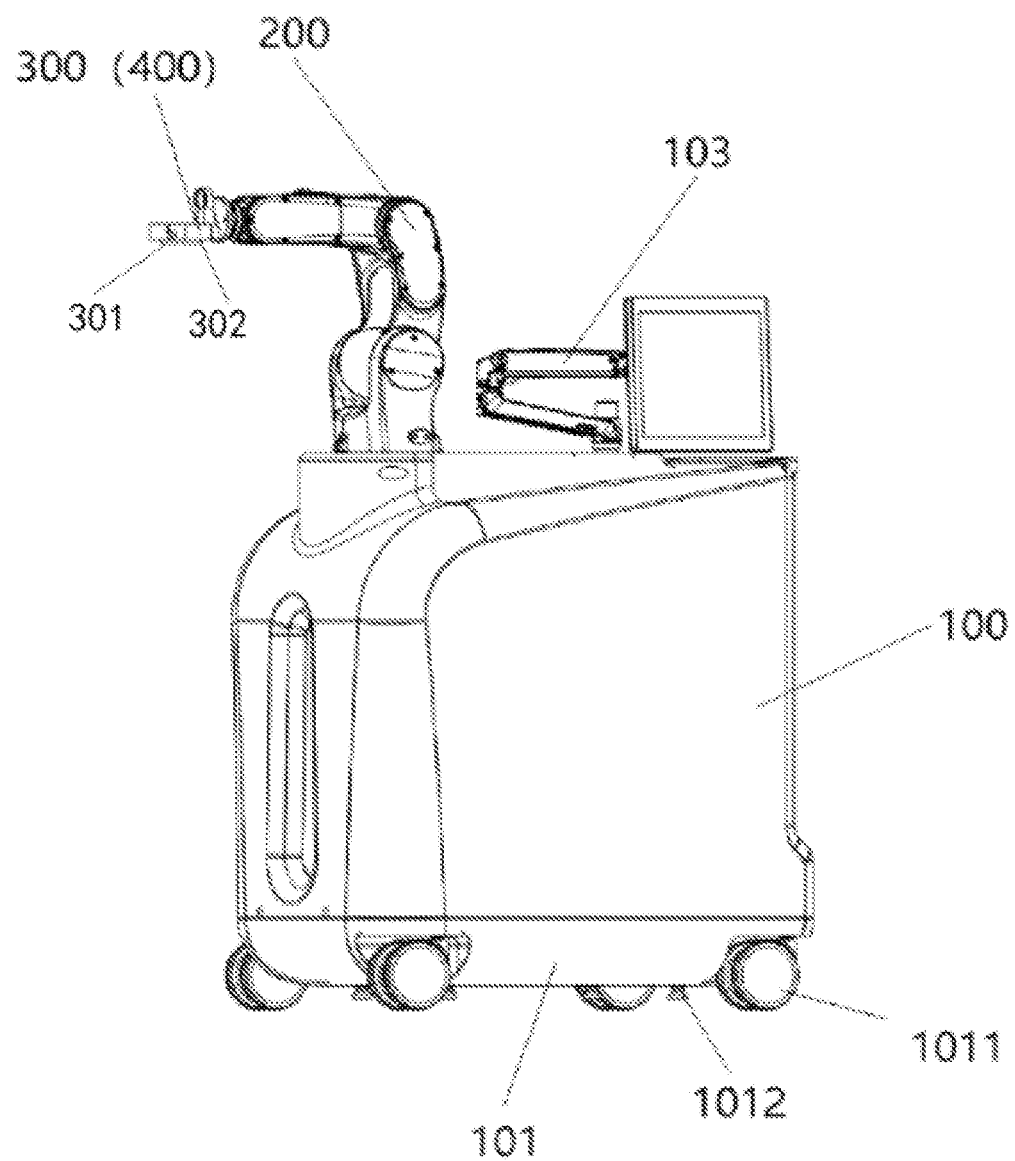
FIG. 3 is a schematic diagram of an embodiment according to a surgical robot system of the present invention in which a state of an end of a robotic arm connected to a scanning module is shown.

With reference to FIG. 3 which shows a structural diagram of an embodiment according to a surgical robot system of the present invention, the system has a workstation 100, a robotic arm 200, a scanning module 300, a guiding module 400 (not shown); wherein the workstation 100 includes a housing 101, a computation and control center 102 (not shown), a touch screen 103 and a pedal which is not shown, and the housing 101 includes four wheels 1011, three fixing apparatuses 1012 and a handle; the robotic arm 200 includes 6 joints and is capable of moving in 6 degrees of freedom, and a force sensor is mounted at an end of the robotic arm to sense and measure applied forces in various dimensions; the scanning module 300 includes a projecting component 301 and an image acquiring apparatus 302, and the projecting component 301 and the image acquiring apparatus 302 have a predetermined relationship of relative spatial position; and the projecting component 301 could emit a specific coded image to the target space and the image acquiring apparatus 302 collects the image, and an accurate three-dimensional structure of the target space is acquired by a corresponding decoding algorithm for the subsequent registration. The projecting component 301 includes a light source, a lens group, a digital micromirror device and a control module. The image acquiring apparatus 302 is a camera. The projecting component 301 may not only emit a specific coded image but also project an image to the target space. For example, important physiological information of the patient, such as heartbeat, blood pressure and blood type, is projected onto the surface of the patient's skin to display the information in a non-contact and safe manner, and distortion correction may also be performed. The wheel 1011 may be a universal one, which is convenient to move. After the device is moved to an appropriate position, three fixing apparatuses 1012 go down to replace the wheel 1011 and play a supporting function so as to fix the surgical robot system to the appropriate position. The position of the end of the robotic arm 200 may be determined in real time in the coordinate system of the robotic arm. The position of the scanning module 300 is fixed relative to the position of the end of the robotic arm 200 so as to acquire the position of the scanning module 300 in the space. During the using process, a guiding module is used to replace the scanning module 300 after the registration have been completed by the scanning module 300.

Embodiment 2

Figure 4:
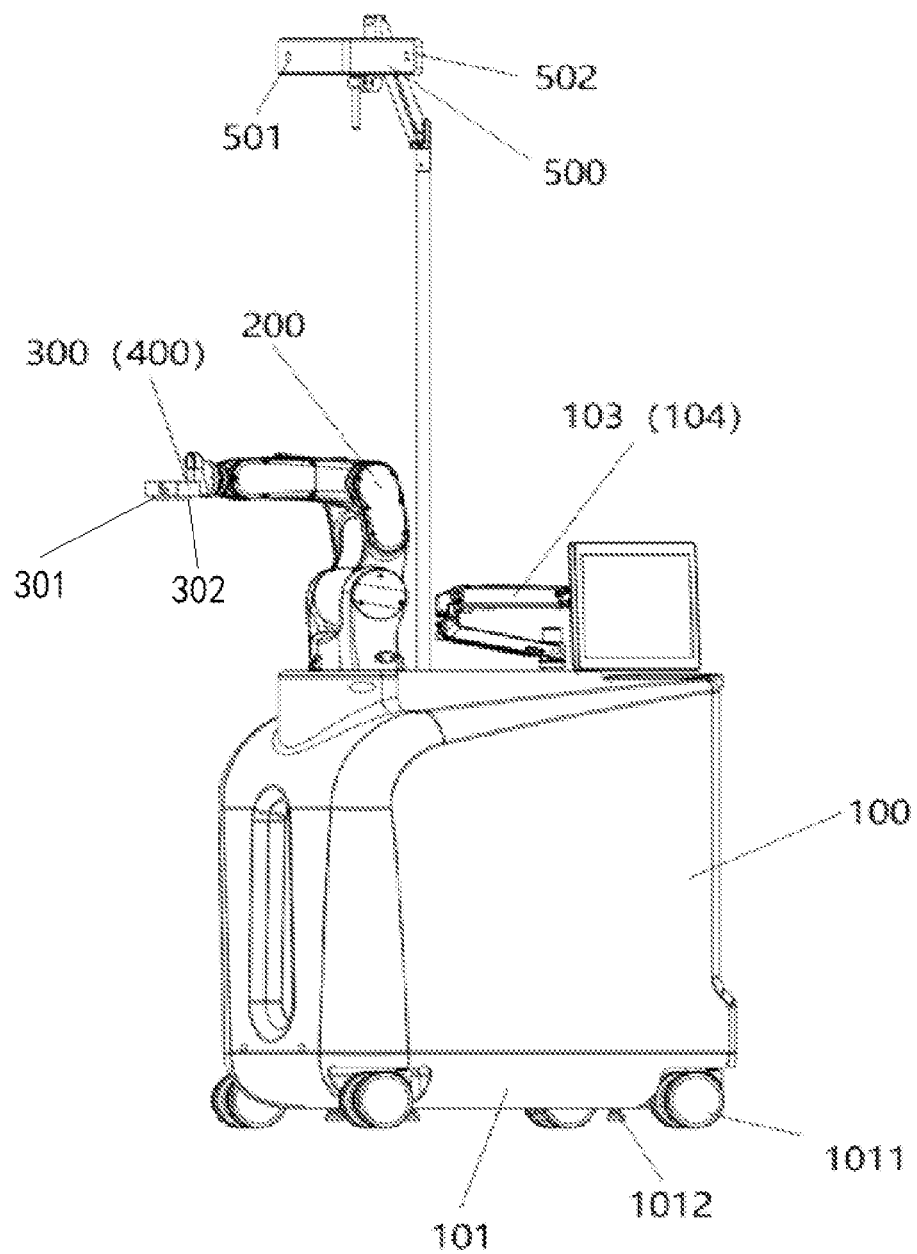
FIG. 4 shows another embodiment according the present invention in which the surgical robot system further includes a tracking module.
Figure 5:
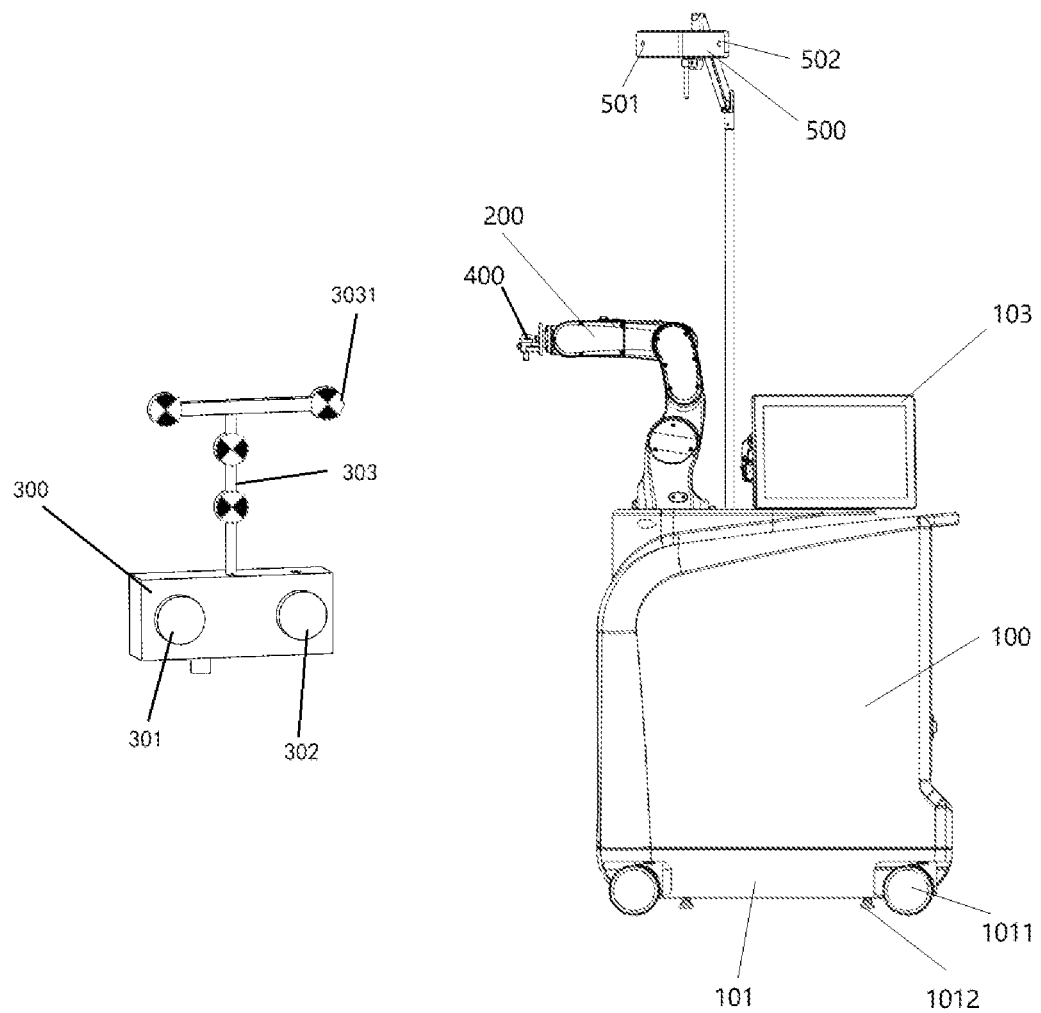
FIG. 5 shows yet another embodiment according to the present invention in which the surgical robot system includes a tracking module and a scanning module which acts as a standalone accessory.

With reference to FIG. 4 which shows a structural diagram of another embodiment according to a surgical robot system of the present invention, the system has a workstation 100, a robotic arm 200, a scanning module 300, a guiding module 400 (not shown) and a tracking module 500; wherein the workstation 100 includes a housing 101, a computation and control center 102 (not shown), a touch screen 103 and a pedal which is not shown, and the housing 101 includes four wheels 1011, three fixing apparatuses 1012 and a handle; the robotic arm 200 includes 6 joints and is capable of moving in 6 degrees of freedom, and a force sensor is mounted at the end of the robotic arm to sense and measure applied forces in various dimensions; the scanning module 300 includes a projecting component 301 and an image acquiring apparatus 302, and the projecting component 301 and the image acquiring apparatus 302 have a predetermined relationship of relative spatial position; and the projecting component 301 may emit a specific coded image to the target space and the image acquiring apparatus 302 collects the image, and an accurate three-dimensional structure of the target space is acquired by a corresponding decoding algorithm for the subsequent registration. The projecting component 301 includes a light source, a lens group, a digital micromirror device and a control module. The image acquiring apparatus 302 is a camera. The projecting component 301 may not only emit a specific coded image but also project an image to the target space. For example, important physiological information of the patient, such as heartbeat, blood pressure and blood type, is projected onto the surface of the patient's skin to display the information in a non-contact and safe manner, and distortion correction may also be performed. The wheel 1011 may be a universal wheel, which is convenient to move. After the device is moved to an appropriate position, three fixing apparatuses 1012 go down to replace the wheel 1011 and play a supporting function so as to fix the surgical robot system to the appropriate position. The tracking module 500 may track the position of the scanning module 300. The scanning module 300 includes a traceable structure, which is shown in FIG. 5 but not in FIG. 4, for example, a self-luminous spherical marker or a special structure consisting of corner point patterns. The tracking module may be a binocular camera, i.e., both 501 and 502 are cameras. The tracking module may also be a structure combining the binocular camera with an infrared light emitting device. At this moment, the scanning module 300 includes a light-traceable structure consisting of spherical markers which may reflect infrared light. The traceable structure may also be connected to the end of the robotic arm so as to position the end of the robotic arm or correct the position thereof.

Embodiment 3

With reference to FIG. 5 which shows a structural diagram of yet another embodiment according to a surgical robot system of the present invention, the system has a workstation 100, a robotic arm 200, a scanning module 300, a guiding module 400 and a tracking module 500; wherein the workstation 100 includes a housing 101, a computation and control center 102 (not shown), a touch screen 103 and a pedal which is not shown, and the housing 101 includes four wheels 1011, three fixing apparatuses 1012 and a handle, the wheel 1011 may be a universal wheel, which is convenient to move, wherein in response to that the device is moved to an appropriate position, three fixing apparatuses 1012 go down to replace the wheel 1011 and play a supporting function so as to fix the surgical robot system to the appropriate position; the robotic arm 200 includes 6 joints and is capable of moving in 6 degrees of freedom, and a force sensor is mounted at the end of the robotic arm to sense and measure applied forces in various dimensions; as an independent part, the scanning module 300 includes a projecting component 301, an image acquiring apparatus 302, and a traceable structure 303, and the traceable structure 303 includes 4 traceable corner points 3031. A guiding module 400 may be connected to an end of the robotic arm via a flange. The guiding module 400 includes a through hole through which another surgical instrument such as a guide wire, a drill bit, an electrode or the like may be guided and positioned. The tracking module 500 is a binocular camera (501 and 502). The scanning module 300 may be handheld to scan the target space, and the tracking module 500 tracks the position of the scanning module in real time so as to convert the scanned image in the coordinate system of the robotic arm for registration, and therefore, the robotic arm 200 is controlled by the workstation 100 to move along a preset path; as the tracking module 500 may also track the position of the guiding module 400, a traceable structure similar to 303 is mounted on the guiding module 400, as a correction reference or an independent positioning method for determining the position of the guiding module 400.

Embodiment 4

Figure 6:
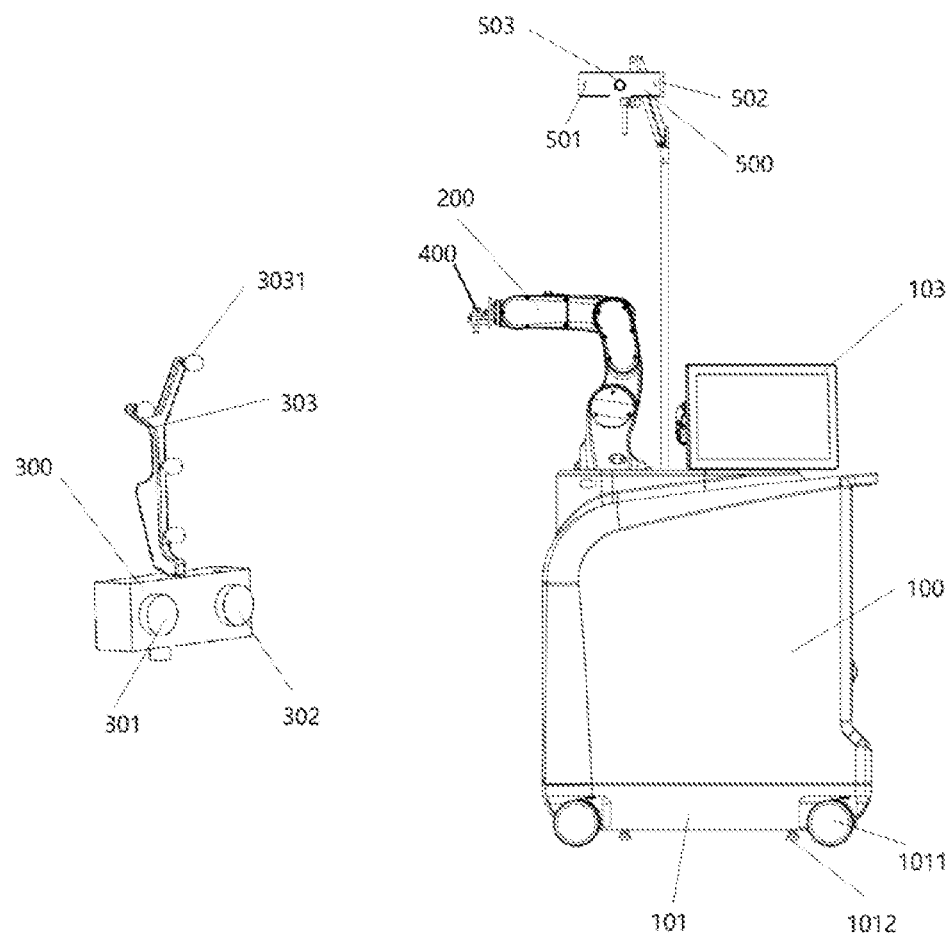
FIG. 6 shows another embodiment according to the present invention in which the surgical robot system includes a tracking module and a scanning module which acts as a standalone accessory.

With reference to FIG. 6 which shows a structural diagram of another embodiment according to a surgical robot system of the present invention, the system has a workstation 100, a robotic arm 200, a scanning module 300, a guiding module 400 and a tracking module 500; wherein the workstation 100 includes a housing 101, a computation and control center 102 (not shown), a touch screen 103 and a pedal which is not shown, and the housing 101 includes four wheels 1011, three fixing apparatuses 1012 and a handle; the wheel 1011 may be a universal wheel, which is convenient to move, and in response to that the device is moved to an appropriate position, three fixing apparatuses 1012 go down to replace the wheel 1011 and play a supporting function so as to fix the surgical robot system to the appropriate position; the robotic arm 200 includes 6 joints and is capable of moving in 6 degrees of freedom, and a force sensor is mounted at an end of the robotic arm to sense and measure applied forces in various dimensions; as an independent part, the scanning module 300 includes a projecting component 301, an image acquiring apparatus 302, and a light-traceable structure 303, and the light-traceable structure 303 includes 4 light-traceable spherical markers 3031. A guiding module 400 may be connected to an end of the robotic arm via a flange. The guiding module 400 includes a through hole through which another surgical instrument such as a guide wire, a drill bit, an electrode or the like may be guided and positioned. The tracking module 500 is a structure combining a binocular camera (501 and 502) and an infrared emitting apparatus 503. The infrared emitting apparatus 503 emits infrared rays and irradiates to the spherical marker 3031 which may reflect infrared rays. If the light reflected by the spherical marker 3031 is acquired by the binocular camera, the spatial coordinates of the scanning module 300 may be calculated. The scanning module 300 may be handheld to scan the target space, and the tracking module 500 tracks the position of the scanning module in real time so as to convert the scanned image in the coordinate system of the robotic arm, and therefore, the robotic arm 200 is controlled by the workstation 100 to move along a preset path; the tracking module 500 may also track the positions of the guiding module 400 and the robotic arm 200, i.e., a traceable structure similar to 303 is mounted on the guiding module 400 and the robotic arm 200, as a correction reference or an independent positioning method.

Embodiment 5

Figure 7:
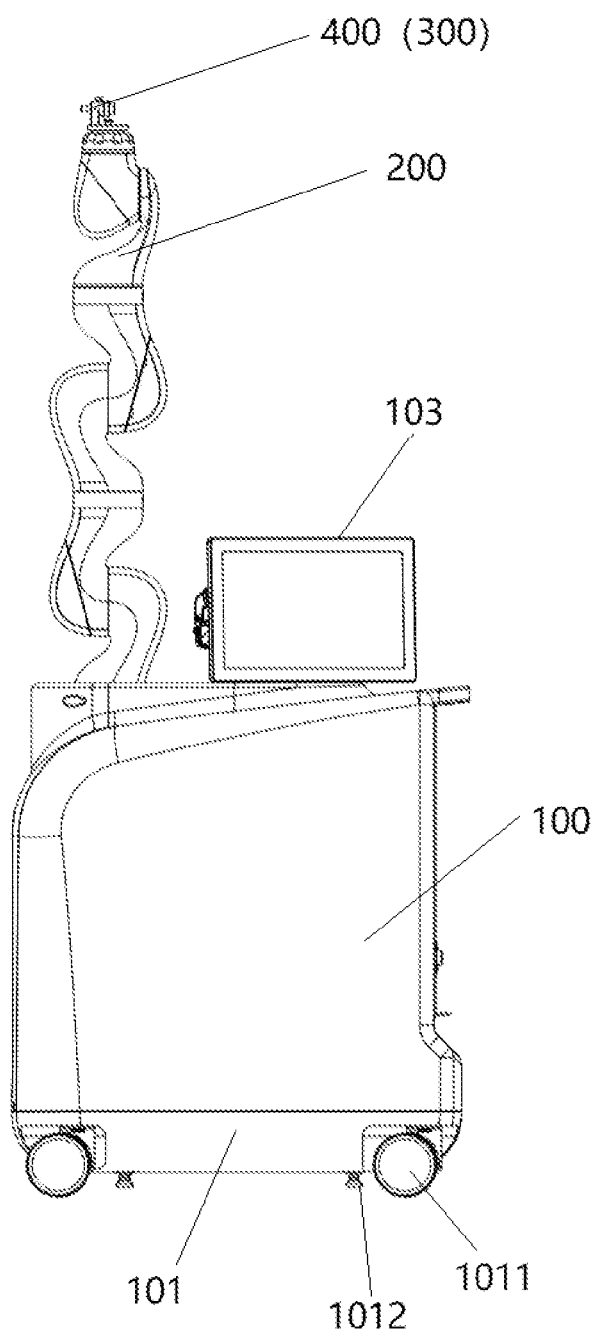
FIG. 7 shows an embodiment of the present invention in which the surgical robot system includes a robotic arm having seven degrees of freedom.
Figure 8:
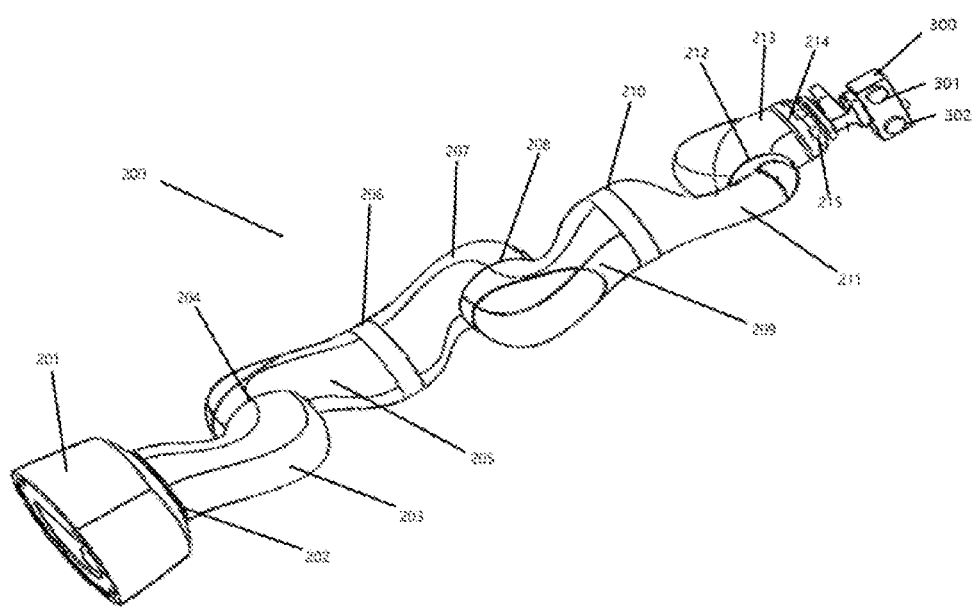
FIG. 8 is an enlarged view of the robotic arm connected to a scanning module in FIG. 7.

With reference to FIG. 7 which shows yet another embodiment of the surgical robot system of the present invention, the system is basically the same as that in embodiment 1. The difference is that the robotic arm 200 has 7 degrees of freedom. An enlarged view of the robotic arm 200 connected to the scanning device 300 is shown in FIG. 8. The robotic arm includes a base 201, a first joint 202, a first arm segment 203, a second joint 204, a second arm segment 205, a third joint 206, a third arm segment 207, a fourth joint 208, a fourth arm segment 209, a fifth joint 210, a fifth arm segment 211, a sixth joint 212, a sixth arm segment 213, a seventh joint 214, a seventh arm segment 215 (the end of the robotic arm); each joint is provided with a torque sensor; and the robotic arm 200 is mounted to the workstation 100 via the base 201. The scanning module 300 includes a projecting component 301 and an image acquiring apparatus 302.

Embodiment 6

Figure 9:
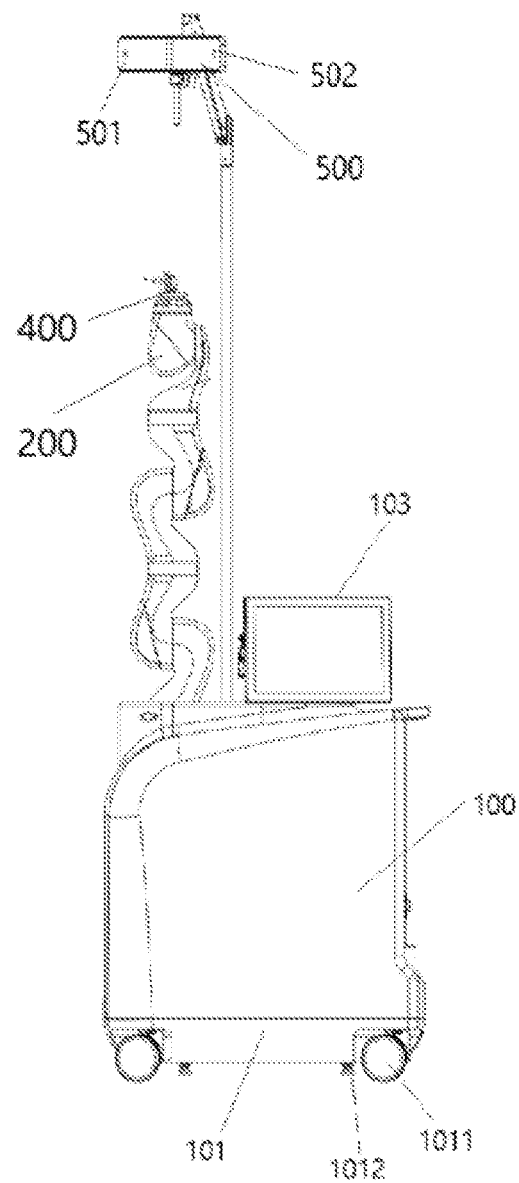
FIG. 9 shows yet another embodiment according to the present invention in which the surgical robot system includes a tracking module and a robotic arm having seven degrees of freedom.

With reference to FIG. 9 which shows another embodiment of the surgical robot system of the present invention, the system is basically the same as that in embodiment 2. The difference is that the robotic arm 200 has 7 degrees of freedom. There is a motor at the joint of the robotic arm. The force applied to the robotic arm 200 may be calculated with the value of the current in the motor. Under some circumstances, the joint may also have a torque sensor for sensing and measuring the applied forces.

Embodiment 7

Figure 10:
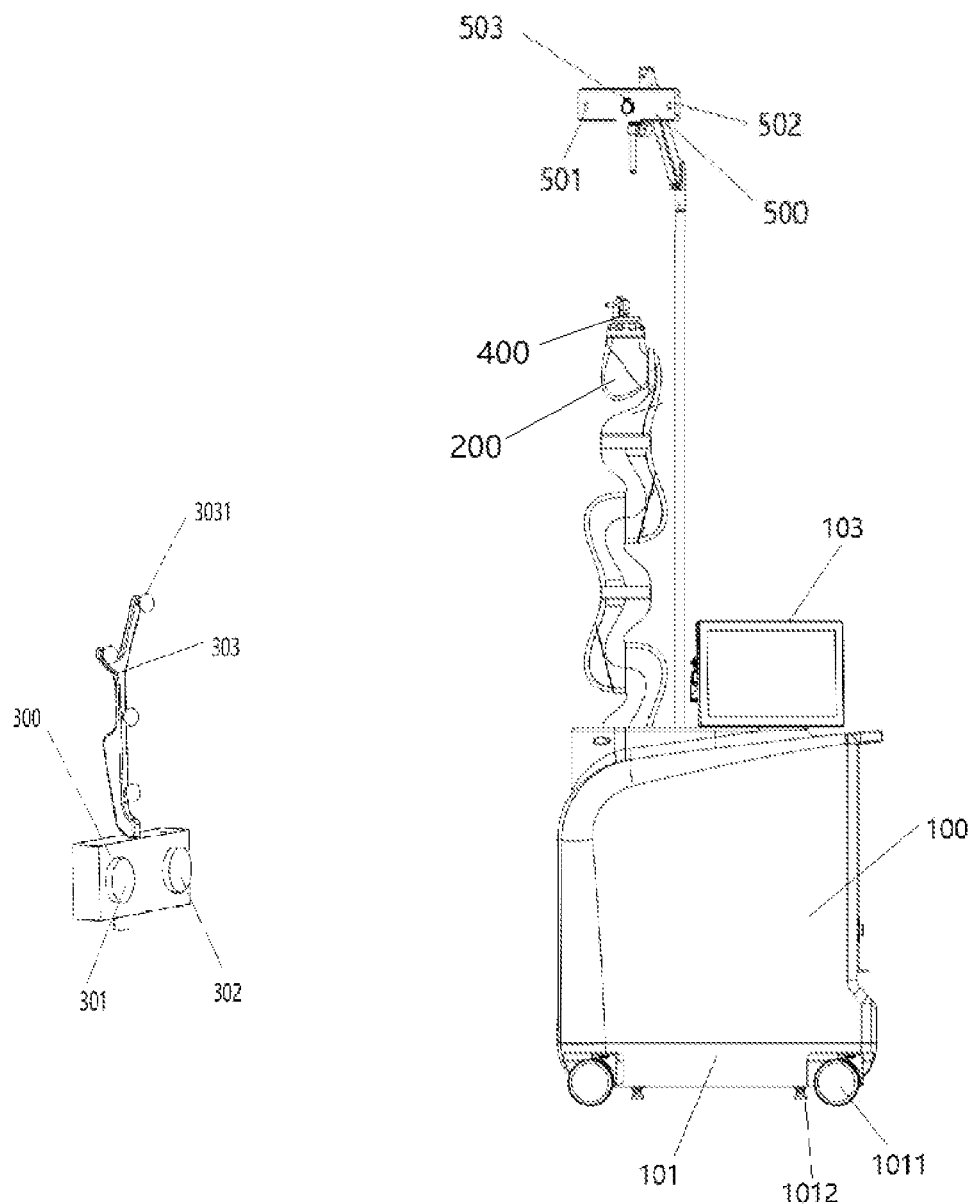
FIG. 10 shows another embodiment of the present invention in which the surgical robot system includes a tracking module, a standalone scanning module and a robotic arm having seven degrees of freedom.

With reference to FIG. 10 which shows another embodiment of the surgical robot system of the present invention, the system is basically the same as that in embodiment 4. The difference is that the robotic arm 200 has 7 degrees of freedom. In the embodiment, the scanning module and the tracking module which are the same as those in embodiment 3 may be adopted, i.e., a corner point may be adopted as a traceable marker, and a binocular camera is used for collecting images.

The surgical robot system of the invention may be used in a variety of surgical situations and has different using methods. Only some of the examples are shown below.

Embodiment 8

An embodiment of the method for using the surgical robot system according to embodiment 1, the method comprising the following steps:

A) receiving medical image data, such as magnetic resonance image data, functional magnetic resonance image data, CT image data, phase contrast magnetic resonance angiography (PC-MRA) data and the like by the workstation 100 of the surgical robot system through the interface, and preferably unifying formats of the surgical data, and afterwards constructing a three-dimensional model of the target space by a software, "Neurosurgery Robot Planning Software", which is pre-loaded in the workstation 110, wherein blood vessels are displayed in the three-dimensional model, and the user plans a surgical solution according to a planning guide provided by the software and determines the path of the surgical instrument;

B) fixing the workstation 100 to an appropriate position, sending by a user an instruction through the input device 104, for example, a mouse or a keyboard, to make the robotic arm 200 control the scanning device 300 connected to the flange, projecting structural light to a target space by the projecting component, collecting the image by the camera and calculating a three-dimensional structure of the target space based on the decoding of the coded images, wherein, preferably, the software of the workstation 100 may control the robotic arm 200 to adjust the position based on the range of the collected images until a three-dimensional structure which meets with the requirements is acquired after data is collected a plurality times, and then registration a three-dimensional structure of the surgical area with the three-dimensional model in step A; and C) performing a surgical operation after the registration is completed, and performing the following steps in an operation in which a deep electrode is placed: replacing the scanning module 300 with the guiding module 400, sending an instruction to the robotic arm 200 by the workstation 100 according to the surgical plan made in step A, the robotic arm 200 moving to a specified position, determining a direction and a position for the drill bit of the surgical drill by the user via the guiding module 400, mounting surgical accessories such as a limiting stopper based on the parameters provided by the Neurosurgery Robot Planning Software, then, making a hole in a surgical site, for example, a head, and then using another surgical instrument such as a guide wire or an electrode to replace the drill bit, and going forward along a channel of an orienting device to reach a specified position. If it is a multi-step operation, the robotic arm may be dragged to a desired position to complete the operation with the step in accordance with the pre-determined operation plan. The process shall be repeated many times till all planned steps are completed.

Embodiment 9

Figure 11:
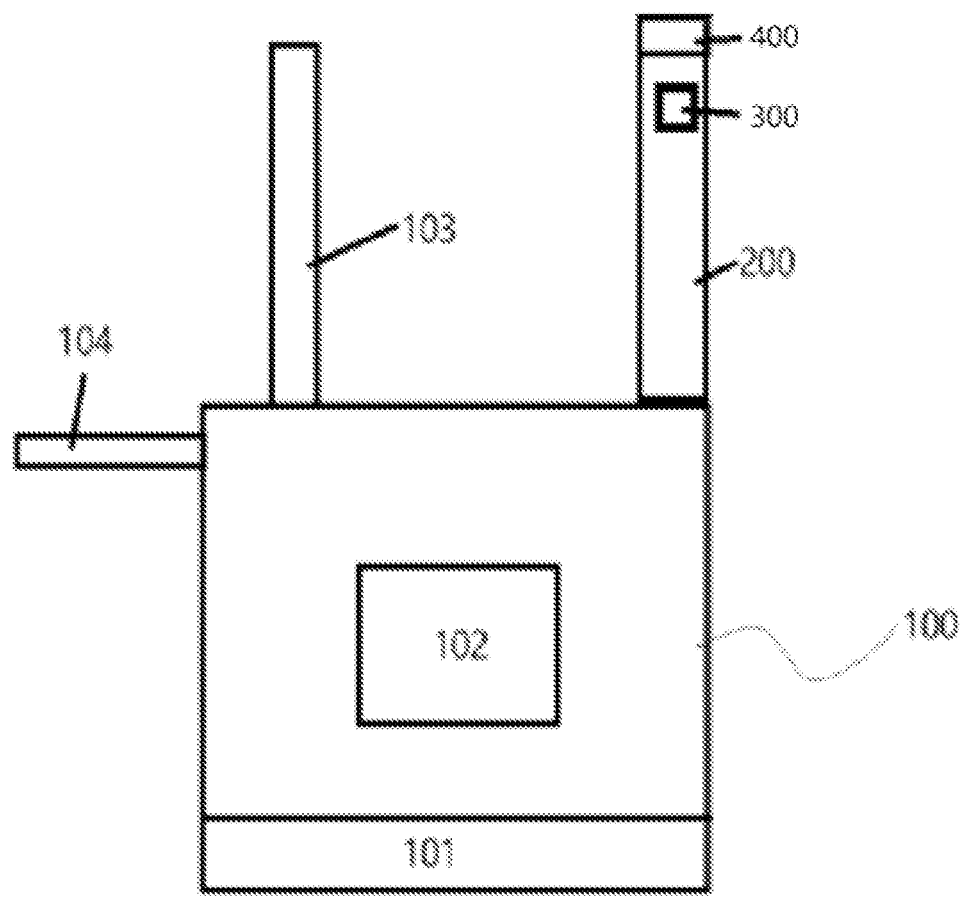
FIG. 11 shows a schematic diagram of yet another embodiment of the present invention in which a scanning module is integrated in a robotic arm.

With reference to FIG. 11, the numbers and references in another embodiment of the present invention is the same as those in FIG. 1. The difference is that the scanning module 300 is integrated in the robotic arm 200, and preferably to the end of the robotic arm, which ensures that the scanning module has sufficient degrees of freedom, for the convenience of adjusting angles. During the process of using the surgical robot, the guiding module 400 is sterilized according to the needs. The scanning module 300 is generally not suitable for high temperature disinfection as it has electronic components. However, as the scanning module 300 is integrated to the robotic arm in the embodiment, the description is different from that in FIG. 1. It is not necessary to remove the scanning module 300 from the flange when the guiding module 400 is mounted. The robotic arm 200 with the flange and the scanning module 300 is wrapped with a sterile cloth. And then, the sterilized guiding module 400 is mounted on the flange, and sterilized surgical tools are used to continue the operation.

Embodiment 10

An example of the method for using the surgical robot system in embodiment 9 is basically the same as that in embodiment 7. The difference is that the scanning module is integrated in an end of the robotic arm. As a result, the difference is that the guiding apparatus is connected directly to the robotic arm via the flange after the registration without occupying the flange.

In the description of the embodiments of the present invention, unless otherwise explicitly defined or limited, the terms "mounted", "connected with", and "connected to" should be interpreted broadly. For example, they may refer to a fixed connection, detachable connection or integrated connection, or may be a mechanical connection or electrical connection, or may refer to a direct connection or an indirect connection via an intermediary, or may be an internal communication of two elements. For those of ordinary skill in the art, the specific meanings of the above-mentioned terms in the present invention may be understood according to specific situations.

Finally, it should be noted that the above-mentioned embodiments are only specific implementations of the present invention, which are used to illustrate the technical solutions of the present invention and shall not be construed as limitation. The protection scope of the present invention is not limited thereto. Although referring to the foregoing embodiments to make a detailed description for the present invention, those of ordinary skill in the art should understand that: for any person skilled in the art, modifications may still be made to the technical solutions described in the foregoing embodiments within the technical scope disclosed in the present invention, or changes may be easily conceived, or equivalent substitutions may be made for some of the technical features; these modifications, changes or substitutions do not deviate the nature of the corresponding technical solutions from the spirit and scope of the technical solutions of the embodiments of the present invention, and should fall within the protection scope of the present invention. Therefore, the protection scope of the present invention should be subject to the protection scope of the claims.

What is claimed is:

1. A surgical robot system, comprising:
a workstation 100, comprising a housing 101 having four wheels 1011, three fixing apparatuses 1012 and a handle, a computation and control center 102, a display apparatus 103 and an input device 104, wherein the four wheels 1011 are able to move; after robot system is moved to a position, three fixing apparatuses 1012 go down to replace the wheel 1011 and play a supporting function so as to fix the surgical robot system to the position; and the display apparatus 103 is configured to display a three-dimensional image and a software control interface generated by the computation and control center 102;

a robotic arm 200, comprising a plurality of arm segments which are connected by joints, wherein the robotic arm 200 includes a base 201, a first joint 202, a first arm segment 203 on a right of the base 201, a second joint 204 left to the first arm segment 203, a second arm segment 205 on a left of the base 201, a third joint 206 with one end connected to the second arm segment 205; a third arm segment 207 on the left, a fourth joint 208, a fourth arm segment 209 on the right, a fifth joint 210 with one end connecting to the fourth arm segment 209, a fifth arm segment 211 on the right connecting to the other end of the fifth joint 210, a sixth joint 212, a sixth arm segment 213 on the left, a seventh joint 214, a seventh arm segment 215 on the left which is the end of the robotic arm; each joint is provided with a torque sensor; and the robotic arm 200 is mounted to the workstation 100 via the base 201;

a scanning module 300, configured to collect information for a target space, wherein the scanning module 300 includes a projecting component 301, an image acquiring apparatus 302, and a traceable structure 303, and the traceable structure 303 includes 4 traceable corner points 3031, wherein the scanning module 300 is connected to the robotic arm 200 in a detachable manner; wherein the projecting component 301 and the image acquiring apparatus 302 have a predetermined relationship of relative spatial position; and the projecting component 301 emits a specific coded image to a target space and the image acquiring apparatus 302 collects the image, and an accurate three-dimensional structure of the target space is acquired by a corresponding decoding algorithm for the subsequent registration; the projecting component 301 includes a light source, a lens group, a digital micromirror device and a control module; the image acquiring apparatus 302 is a camera; the projecting component 301 not only emits a specific coded image but also projects an image to the target space; and a guiding module 400, configured to guide a surgical instrument to move in a desired trajectory, wherein the guiding module 400 is connected to an end of the robotic arm via a flange; wherein the guiding module 400 includes a through hole through which another surgical instrument including a drill bit is guided and positioned, wherein information collected by the scanning module 300 is processed by the workstation to acquire three-dimensional information of the target space;

a tracking module 500, wherein the tracking module 500 is a position tracking module configured to track a position of the scanning module, and the position tracking module is an optical tracking apparatus which includes a light-traceable marker, a camera unit and a light emitting unit; the light is infrared rays; the marker is fixed to the scanning module; in this way, the position of the scanning module is monitored in real time by the optical tracking apparatus;

wherein the robotic arm 200 is controlled by the workstation 100 to move along a preset path; the tracking module 500 tracks positions of the guiding module 400 and the robotic arm 200 by a traceable structure 303 mounted on the guiding module 400 and the robotic arm 200 as a correction reference; and the computation and control center 102 is disposed on top of the housing 101; the computation and control center 102 communicates with the display apparatus 103, the input device 104, the tracking module 500 and the robotic arm 200, the robotic arm 200 communicates with the scanning module 300 and the guiding module 400; and the tracking module 500 is disposed between the display apparatus 103 and the robotic arm 200; and the display apparatus 103, the tracking module 500 and the robotic arm 200, the scanning module 300 and the guiding module 400 are disposed on top of the computation and control center 102.

2. The system according to claim 1, wherein a position of the scanning module 300 in a coordinate system of the robotic arm 200 is determined by the robotic arm.

3. A method for using the surgical robot system according to claim 1, comprising the following steps:

a) using the surgical robot system to receive image data for visualized display, and making a surgical plan in the three-dimensional model;

b) using the scanning module to scan a target space, generating a three-dimensional structure with scanned data via the workstation, and registration with the image acquired in step a; and c) mounting the guiding module at an end of the robotic arm and executing the predetermined surgical plan.

* * * * *